United States Patent [19]

Hanada et al.

[11] Patent Number: 4,801,538
[45] Date of Patent: Jan. 31, 1989

[54] PROCESS FOR DETERMINING SUPEROXIDE DISMUTASE ACTIVITY

[75] Inventors: Toshiro Hanada, Kawagoe; Kazuhiko Yamanishi, Tokyo, both of Japan

[73] Assignee: Wako Pure Chemical Industries, Ltd., Osaka, Japan

[21] Appl. No.: 834,971

[22] Filed: Feb. 28, 1986

[30] Foreign Application Priority Data

Mar. 1, 1985 [JP] Japan ................................ 60-40526
Jun. 29, 1985 [JP] Japan ............................... 60-144168
Nov. 26, 1985 [JP] Japan ............................... 60-265257

[51] Int. Cl.$^4$ ................ C12Q 1/26; C12Q 1/28; C12N 9/02; C12N 9/08
[52] U.S. Cl. ................................... 435/25; 435/4; 435/28; 435/189; 435/192
[58] Field of Search .................. 435/25, 4, 28, 189, 435/192; 604/20

[56] References Cited

U.S. PATENT DOCUMENTS 4,384,042 5/1983 Miike et al. ................................ 435/25

FOREIGN PATENT DOCUMENTS 1182061 2/1985 Canada ................................ 435/189
6024199 7/1983 Japan ................................... 435/25
2089979 6/1982 United Kingdom ............... 435/4
2089980 6/1982 United Kingdom .

OTHER PUBLICATIONS

Chemical Abstracts, vol. 102, No. 1, Jan. 7, 1985, pp. 415, 416, Abstract No. 4350M.

Primary Examiner—Robert J. Warden
Assistant Examiner—Janelle Graeter
Attorney, Agent, or Firm—Armstrong, Nikaido, Marmelstein & Kubovcik

[57] ABSTRACT

Superoxide dismutase activity is determined by measuring hydrogen peroxide produced by using superoxide anion as a substrate and acting superoxide dismutase thereon in the presence of an electron carrier. When maleimide or a derivative thereof, and if necessary, a carbonyl compound, and if further necessary bromine ions and/or citric acid or a salt thereof are added to the electron carrier, the sensitivity and the linearity of calibration curves are further improved.

15 Claims, 12 Drawing Sheets

F I G. 7
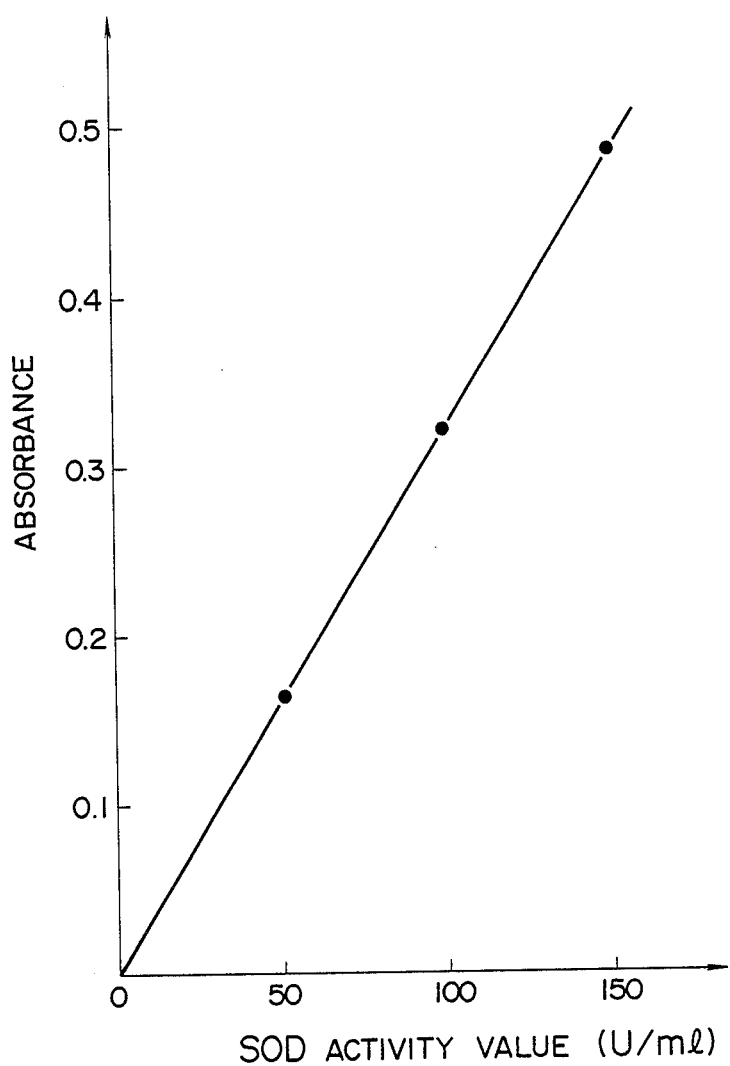

PROCESS FOR DETERMINING SUPEROXIDE DISMUTASE ACTIVITY

BACKGROUND OF THE INVENTION

This invention relates to a process for determining superoxide dismutase (hereinafter abbreviated to SOD) contained in body fluids, for example, serum and the like.

In the natural world, aerobic living things such as microorganisms, plants and higher animals efficiently obtain energy indispensable for maintenance of their life by utilizing molecular oxygen effectively. It is known that simultaneously with the utilization, various active oxygens are produced and do a variety of injuries to the living bodies. For example, superoxide anion (hereinafter referred to as $O_2^-$), which is one of the active oxygens, is extensively harmful to living bodies: for example, it causes inflammation, carcinogenesis, aging, denaturation of nucleic acids, enzymes, lipids and the like.

SOD exists universally in all aerobic living things, is called also superoxide-dismutation enzyme, is an enzyme catalyzing dismutation reaction of $O_2^-$ in the living bodies, i.e. $2O_2^- + 2H^+ \rightarrow O_2 + H_2O_2$, and protects the living bodies against the toxicity of oxygen.

There are various reports on assay of SOD activity in erythrocyte, leukocyte and tissue slice and on its clinical significance. No sufficient investigation on SOD in serum has been conducted yet because various components such as protein components affect SOD measured values. All the SOD activity determination processes now employed comprise a system for producing $O_2^-$ and a system for detecting $O_2^-$ and utilize a decrease of the produced amount of $O_2^-$ due to acceleration of dismutation of $O_2^-$ by SOD.

As the system for producing $O_2^-$ in the SOD activity determination processes, there are also, for example, a system in which $O_2^-$ is produced by using a superoxidized compound, e.g., potassium superoxide, and a system in which $O_2^-$ is produced by reaction of a reduced form coenzyme and an electron carrier. Now there is generally employed a process which mainly comprises acting xanthine oxidase on xanthine. This reaction is shown below:

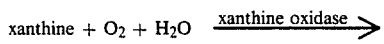

$$\text{uric acid} + 2H^+ + O_2^-.$$

As the system for detecting $O_2^-$, there is, for example, the nitro blue tetrazolium (hereinafter abbreviated to $NO_2$-TB) method and the cytochrome c method which utilize the reducing action of $O_2^-$, and the epinephrine method, pyrogallol method and 6-hydroxydopamine method which utilize the oxidizing action of $O_2^-$.

The principle of these SOD activity determination processes is shown in the following formulae by taking the case of a process using xanthine and xanthine oxidase in the $O_2^-$ production system and the $NO_2$-TB method in the $O_2^-$ detection system:

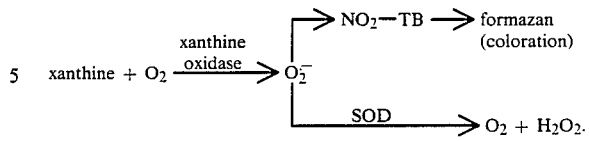

That is to say, in the $O_2^-$ production system, xanthine oxidase, for example, catalyzes the reaction of xanthine with molecular oxygen ($O_2$) to give $O_2^-$, and when SOD is present in the system, dismutation of $O_2^-$ is accelerated and $O_2^-$ produced becomes $O_2$ and $H_2O_2$. $O_2^-$ produced here reduces cytochrome c, $NO_2$-TB or the like to subject the same to coloration and oxidizes epinephrine, pyrogallol, 6-hydroxydopamine or the like to subject the same to coloration. Therefore, by utilizing this property, a decrease in absorbance of sample with respect to reagent blank value is measured and SOD activity value is determined. Accordingly, all of these processes are disadvantageous, for example, in that since the reagent blank value is high, the precision of determination is insufficient and the range of determination is narrow. Therefore, there has been desired the advent of an SOD activity determination process which is improved in these points, has higher precision, and has a wider determination range.

SUMMARY OF THE INVENTION

This invention aims at providing a novel and very useful SOD activity determination process free from the defects of conventional SOD activity determination process comprising measuring a decrease in absorbance of sample with respect to reagent blank value, namely, low precision of determination, narrow determination range, etc. due to high reagent blank value.

This invention provides a process for determining SOD activity by use of $O_2^-$ as a substrate which comprises making a quantitative determination of the hydrogen peroxide produced by the action of SOD on the $O_2^-$ in the presence of an electron carrier.

Further, this invention provides an SOD activity determination process according to the above-mentioned SOD activity determination process, wherein the procedure is carried out in the presence of the electron carrier and maleimide or a maleimide derivative or in the presence of the electron carrier and maleimide or a maleimide derivative and a carbonyl compound.

In addition, this invention provides an SOD activity determination process according to the latter of the SOD activity determination process described above, wherein the procedure is carried out in the presence of the electron carrier, maleimide or a derivative thereof, a carbonyl compound and bromine ion and/or citric acid or a salt thereof.

BRIEF DESCRIPTION OF THE DRAWINGS

FIG. 7 shows a calibration curve obtained in Example 11.

DESCRIPTION OF THE PREFERRED EMBODIMENTS

Figure 1:
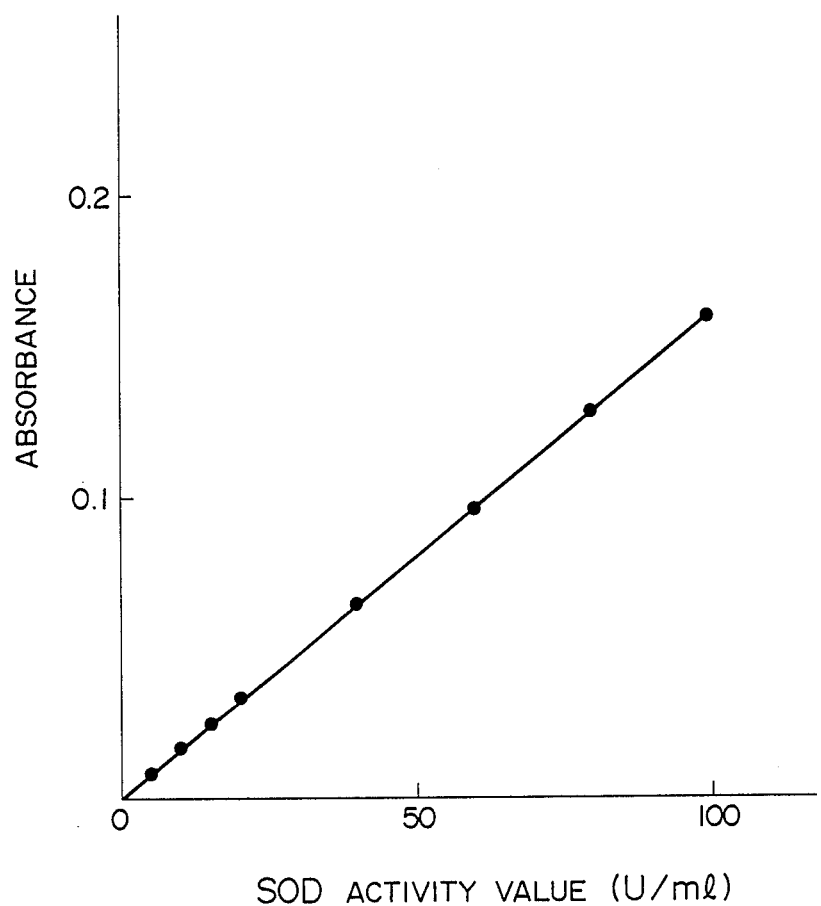
FIG. 1 shows a calibration curve obtained in Example 1.

Usually, $O_2^-$ changes gradually to hydrogen peroxide (hereinafter referred to as $H_2O_2$) owing to dismutation reaction of itself. However, the present inventors have first found the fact that unexpectedly, no $H_2$; $O_2$ production by spontaneous dismutation reaction of $O_2^-$ itself occurs when an electron carrier is present. Therefore, when SOD is present in the system, $H_2O_2$ is produced in proportion to the amount of the SOD activity. This invention has been accomplished on the basis of this finding, and by virtue of the presence of an electron carrier in the $O_2^-$ production system containing SOD, this invention permits assay of SOD activity by determination of $H_2O_2$ produced in this system. Further, this invention has been accomplished on the basis of the fact, which the present inventors have found for the first time, that in assaying SOD activity by incorporating also an electron carrier into the $O_2^-$ production system containing SOD and determining $H_2O_2$ produced in this system, the reagent blank value and its variation are reduced by the presence of maleimide or a maleimide derivative in the $O_2^-$ production system, and that when a carbonyl compound is also present in addition to maleimide or a derivative thereof in this system, the reagent blank value and its variation are further improved.

In addition, this invention has been accomplished on the basis of the fact, which the present inventors have found for the first time, that in assaying SOD activity by incorporating an electron carrier, maleimide or a maleimide derivative, and a carbonyl compound into the $O_2^-$ production system containing SOD and determining $H_2O_2$ produced in the system, the sensitivity is increased and the linearity of calibration curve is improved when bromine ion is further present in the $O_2^-$ production system, and the linearity of calibration curve extends to a higher concentration range with the same sensitivity when citric acid or a salt thereof is further present in the $O_2^-$ production system.

The electron carrier used in the process of this invention includes, for example, phenazine methosulfate (PMS), 1-methoxy-5-methylphenazinium methylsulfate (1-methoxy PMS), 9-dimethylaminobenzo-α-phenazoxonium chloride (meldola's blue), etc. However, it is not limited to these compounds, and all electron carriers having an action equal to that of these compounds can be used. These compounds may be used alone or as a mixture thereof. Although the concentration of these electron carriers is not critical, a concentration of 0.001 to 1 mM is usually preferably used.

As maleimide or a maleimide derivative used in this invention, there can be used various compounds, for example, maleimide, N-ethylmaleimide (hereinafter abbreviated to NEM), N-(9-acridinyl)maleimide, N-(1-anilinonaphthyl-4)maleimide, N-(4-anilinophenyl)-maleimide, N-[p-(2-benzimidazolyl)phenyl]maleimide, N-(7-dimethylamino-4-methylcumalinyl)maleimide, N-(3fluoranthyl)maleimide, and N-substituted maleimide derivatives of the following general formula [I] disclosed in Japanese Patent Application Kokai (Laid-Open) No. 204171/84:

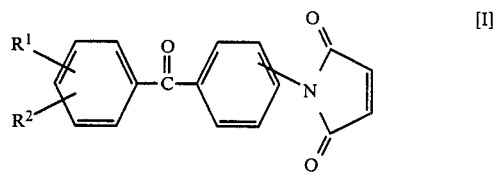

wherein $R^1$ is hydrogen, a nitro group, a di-lower alkylamino group, or a group represented by the formula $R^3$—CONH— in which $R^3$ is a lower alkyl group or a phenyl group; $R^2$ is hydrogen or a nitro group; the maleimide substituent group is at an ortho or para position in relation to the benzoyl substituent group. Among them, NEM is preferably used because it is excellent in stability in water.

Although the concentration of maleimide or a maleimide derivative used in this invention is effective when it is 0.5 mmol/liter or more in the reaction solution, a concentration in the range of 2 to 40 mmol/liter is usually preferably used.

As the carbonyl compound used in this invention, there can be exemplified aromatic ketone compounds, aliphatic ketone compounds, etc. Examples of these compounds are given below. The aromatic ketones include benzophenone, acetophenone, 2-hydroxy-4-methoxybenzophenone-5-sulfonic acid (hereinafter abbreviated to HMBP), benzophenone-2-carboxylic acid, 3,3',4,4'-benzophenonetetracarboxylic acid, o-hydroxybenzophenone, p-hydroxybenzophenone, benzophenone-2,4'-dicarboxylic acid, 2-hydroxy-5-methylbenzophenone, 2'-hydroxy-5'-methylacetophenone, 4'-hydroxy-2'-methylacetophenone, 4'-hydroxy-3'-methylacetophenone, 2'-hydroxy-4'-methoxyacetophenone, 2-hydroxy-4'-methoxyacetophenone, etc. The aliphatic ketones include acetone, methyl ethyl ketone, methyl n-butyl ketone, methyl isobutyl ketone, methyl tert-butyl ketone, methyl n-amyl ketone, methyl isoamyl ketone, etc.

Although the concentration of the carbonyl compound is effective when it is 0.5 mmol/liter or more in the reaction solution, a concentration in the range of 1 mmol/liter to 40 mmol/liter is usually preferably used.

Although the concentration of bromine ion used in this invention is not critical, a concentration of 0.05 ionic milliequivalent/liter to 10 ionic milliequivalents/liter is usually preferably used. As a bromine ion source, any one may be used so long as it releases bromine ion $Br^-$, though usually, inorganic and organic bromine salts are preferably used. The inorganic bromine salts include, for example, salts such as ammonium bromide, sodium bromide, potassium bromide, lithium bromide, magnesium bromide and the like and other salts obtained by neutralizing hydrobromic acid with an alkaline substance, but are not limited to these salts. The organic bromide salts include, for example, cationic surfactants such as cetyl trimethylammonium bromide, tetramethylammonium bromide, cetyl dimethylethylammonium bromide, cetyl piridinium bromide and the like and compounds obtained by neutralizing hydrobromic acid with an organic basic substance such as an amine, but are not limited thereto.

When bromine ion in this invention is replaced by another halogen ion, the effects of this invention cannot be obtained. That is to say, it was confirmed that when another halogen ion was used in place of bromine ion, adverse effects were brought about, for example, calibration curve was curved at many points, or no coloration occurred, so that measurement was impossible.

It is a great surprise that thus, only bromine ion among halogen ions can achieve the object of this invention and that other halogen ions have adverse effects.

The amount of citric acid or a salt thereof is not critical and usually used in an amount of 3 to 40 mmol/liter in the $O_2^-$ producing system.

As the salt of citric acid, there can be used salts of alkali metals sch as Na, K, Li, etc, a salt of ammonium ($NH_4-$), etc.

The effects obtained by using citric acid or a salt thereof cannot be obtained even if other organic acids or salts thereof are used instead of citric acid or a salt thereof. For example, hydroxy acids having one or more hydroxy groups other than citric acid, e.g. lactic acid, glycolic acid, tartaric acid, malic acid, α-hydroxybutyric acid, etc. and other organic acids such as acetic acid, succinic acid, maleic acid, malonic acid, etc. do not show such effects and the results are almost the same when these acids are not added. When SOD is high in concentration, linearity of the calibration curve cannot be obtained. The fact that only citric acid or a salt thereof shows such effects among various organic acids is a surprising thing.

The bromine ions and citric acid or a salt thereof can be used together, but a particularly synergic effect is not exhibited in the sensitivity and the linearity of calibration curve.

As the $O_2^-$ production system used in this invention, there is mainly used a system in which $O_2^-$ is produced by the reaction of xanthine with xanthine oxidase, a system in which $O_2^-$ is produced by use of a superoxidized compound (e.g., potassium superoxide), or a system in which $O_2^-$ is produced by the reaction of a reduced form coenzyme with an electron carrier. Needless to say, there can be utilized $O_2^-$ produced by other methods, for example, the reaction of reduced form flavin with $O_2$, reduction of $O_2$ with a low valent transition metal ion, or electrolytic reduction of $O_2$.

Although it is sufficient that the pH of solution for the enzymic reaction is from neutral to alkaline, a pH of 7 to 10 is usually preferably used.

The process of this invention is a process for determining the enzyme activity, in principle, by measuring the amount of $H_2O_2$ produced by the action of SOD in a given period of time. Said process permits also determination by the so-called "rate assay" comprising incorporating an enzymic reaction system with a color reagent which develops color on reaction with $H_2O_2$, and determining SOD activity from a change of absorbance of the developed color per unit time. On the other hand, said process permits also determination by the so-called "end point assay" which comprises conducting the enzymic reaction for a given period of time, and measuring the absorbance after stopping the reaction. In general, the end point assay is often employed when SOD activity is assayed by a manual process. Since the end point assay comprises conducting the enzymic reaction for a given period of time, stopping the reaction, and then quantitating $H_2O_2$ produced, it requires a reaction stopper. In this case, there can be employed either a process comprising conducting the enzymic reaction and coloration reaction for a given period of time, stopping the reaction by addition of a reaction stopper, and then measuring the absorbance, or a process comprising conducting the enzymic reaction for a given period of time, then stopping the enzymic reaction by addition of a reaction stopper and at the same time conducting coloration reaction. However, according to the former process, the enzymic reaction is inhibited by the color reagent or a peroxidase in some cases, therefore the latter process which comprises conducting coloration reaction simultaneously with stopping the enzymic reaction is preferred.

As the reaction stopper, when it is taken into consideration that quantitation of $H_2O_2$ is usually conducted by using peroxidase (POD) and an oxidizable color reagent or by using a reagent consisting of a tetravalent titanium compound and 2-(5-bromo-2-pyridylazo)-5-(N-propyl-N-sulfopropylamino)phenol and/or a salt thereof, a reaction stopper having a pH near neutrality and no influence or coloration of these color reagents is preferred. As a reaction stopper satisfying these requirements, the present inventors employed one compound or a mixture of two or more compounds selected from the group consisting of decylsulfuric acid or a salt thereof, dodecylsulfuric acid or a salt thereof, and dodecylbenzenesulfonic acid or a salt thereof, and found that the problems could be solved by using these reaction stoppers.

As to the concentration of the reaction stopper, the reaction stopper sufficiently performs its function when the concentration is 1.5 mmol/liter or more, though a concentration of 3 to 100 mmol/liter is usually preferably used. Although the pH can freely be selected so that the pH of the final color producing solution meets the optimum conditions of the coloration reaction, a pH of 4 to 9 is usually preferably used in consideration of the stability of POD, the stability of the oxidizable color reagent, the pH suitable for the coloration, etc.

As a method and a reagent for quantitating $H_2O_2$ in the SOD activity determination process of this invention, any conventional method and reagent quantitating $H_2O_2$ may be used. For example, there can be used all methods for quantitating $H_2O_2$ by combination of peroxidase and an oxidizable color reagent, and all of the oxidizable color reagents used in these methods and other reagent for quantitating $H_2O_2$. Such oxidizable color reagents include, for example, oxidizable color reagents consisting of a combination of 4-aminoantipyrine (hereinafter abbreviated to 4-AAP) and a phenolic compound or an N,N-disubstituted aniline series compound, combined reagents of 3-methylbenzothiazolinonehydrazone (MBTH) and an aniline series compound, 2,2'-azinobis(3-ethylbenzothiazoline-6-sulfonic acid) (ABTS), triphenylmethane series leuco coloring materials, benzidine derivatives, o-tolidine derivatives, diphenylamine derivatives, triallylimidazole derivatives, o-phenylenediamine, leucomethylene blue derivatives, etc., but they are not limited thereto. In addition to the methods described above, there can be employed as a method for quantitating $H_2O_2$, for example, a method using a combined reagent of a tetravalent titanium compound and 2-(5-bromo-2-pyridylazo)-5-(N-propyl-N-sulfopropylamino)phenol and/or a salt thereof which has recently been developed as a method using no POD.

For further stabilizing the oxidizable color reagent and its developed color after oxidation and coloration, the presence of $\beta$-cyclodextrin and/or a derivative thereof or of $\gamma$-cyclodextrin and/or a derivative thereof in the solution is sufficient.

With respect to the concentrations of these compounds, a concentration of $\beta$-cyclodextrin of 0.01 to 1.5 wt/vol %, that of $\gamma$-cyclodextrin of 0.1 to 3 wt/vol %, that of $\beta$-cyclodextrin derivative of 0.1 to 5 wt/vol % and that of $\gamma$-cyclodextrin derivative of 0.1 to 5 wt/vol % all in the solution are usually used. Mixtures of two or more of these compounds in any ratio may also be used so long as the concentrations of the compounds are within the above-mentioned ranges.

The cyclodextrin derivative includes, for example, $\beta$—CD(—OH)$_{19}$(ONO$_2$)$_2$
$\beta$—CD(—OH)$_{19.2}$(OPO$_3$H)$_{1.8}$
$\beta$—CD(—OH)$_{19}$(OSO$_3$H)$_2$
$\beta$—CD(—OH)$_{18.5}$(—O—CH$_2$—CO$_2$H)$_{2.5}$
$\beta$—CD(—OH)$_{19.3}$(—O—CH$_2$CH$_2$Ch$_2$—SO$_3$H)$_{1.7}$
$\beta$—CD(—OH)$_{18.5}$(—O—CH$_2$Ch$_2$Ch$_2$—SO$_3$H)$_{2.5}$
$\beta$—CD(—OH)$_{18.0}$(—O—CH$_2$CH$_2$CH$_2$—SO$_3$H)$_{3.0}$
$\beta$—CD(—OH)$_7$(—OCH$_3$)$_{14}$
$\beta$—CD(—OCH$_3$)$_{21}$ but it is not limited to these compounds.

In practicing the process of this invention, a specified amount of serum is added to a specified amount of a buffer solution having a pH of about 7 to about 10 containing, for example, 0.05 to 20 mmol/liter of xanthine and 0.001 to 1 mmol/liter of 1-methoxy PMS (a first reagent solution). After the resulting solution is heated to 37° C., a specified amount of a buffer solution of a pH of about 7 to about 10 containing xanthine oxidase (a second reagent solution) is added so that the concentration of xanthine oxidase in the reaction solution becomes 10 to 200 U/liter. The solution thus obtained is subjected to enzymic reaction at 37° C. for a given period of time. Then, a specified amount of a buffer solution containing a reaction stopper, POD, an oxidizable color reagent and if necessary, $\beta$-(and/or $\gamma$-)cyclodextrin and/or a derivative thereof (a third reagent solution) is added to stop the enzymic reaction and initiate the coloration reaction of $H_2O_2$ produced with the oxidizable color reagent at the same time. After the coloration reaction is conducted at 37° C. for a given period of time, the degree of color development is measured. It is sufficient that the pH of the third reagent solution is properly selected so that the pH of the final color producing solution becomes the optimum pH for coloration of the oxidizable color reagent.

In practicing the process of this invention more effectively, a specified amount of serum is added to a definite amount of a buffer solution of a pH of about 7 to about 10 containing, for example, 0.05 to 20 mmol/liter of xanthine, 0.001 to 1 mmol/liter of an electron carrier, e.g., 1-methoxy PMS, 2 to 40 mmol/liter of maleimide or a maleimide derivative, e.g., NEM and 1 to 40 mmol/liter of a carbonyl compound (a first reagent solution). After the resulting solution is heated to 37° C., a specified amount of a buffer solution of a pH of 7 to 10 containing xanthine oxidase (a second reagent solution) is added so that the concentration of xanthine oxidase in the reaction solution becomes 10 to 200 U/liter. The solution thus obtained is subjected to enzymic reaction at 37° C. for a given period of time. Then, a specified amount of a buffer solution containing a reaction stopper, POD, an oxidizable color reagent and if necessary, $\beta$-(and/or $\gamma$-)cyclodextrin and/or a derivative thereof (a third reagent solution) is added to stop the reaction and initiate the coloration reaction of $H_2O_2$ produced with the oxidizable color reagent at the same time. After the coloration reaction is conducted at 37° C. for a given period of time, the degree of color development is measured. It is sufficient that the pH of the third reagent solution is properly selected so that the pH of the final color producing solution becomes the optimum pH for coloration of the oxidizable color reagent.

In practicing the process of this invention still more effectively, a specified amount of serum is added to a buffer solution of a pH of about 7 to about 10 containing, for example, 0.05 to 20 mmol/liter of xanthine, 0.001 to 1 mmol/liter of an electron carrier, e.g., 1-methoxy PMS, 0.05 to 10 ionic milliequivalents/liter of bromine ion and/or 3 to 40 mmol/liter of citric acid or a salt thereof, 2 to 40 mmol/liter of maleimide or a maleimide derivative, e.g., NEM, and 1 to 40 mmol/liter of a carbonyl compound (a first reagent solution). After the resulting solution is heated to 37° C., a specified amount of a buffer solution of a pH of 7 to 10 containing xanthine oxidase (a second reagent solution) is added so that the concentration of xanthine oxidase in the reaction solution becomes 10 to 200 U/liter. The resulting solution is subjected to enzymic reaction at 37° C. for a given period of time. Then, a specified amount of a buffer solution containing a reaction stopper, POD, an oxidizable color reagent and if necessary, $\beta$-(and/or $\gamma$- )cyclodextrin and/or a derivative thereof (a third reagent solution) is added to stop the enzymic reaction and initiate the color reaction of $H_2O_2$ produced with the oxidizable color reagent at the same time. After the color reaction is conducted at 37° C. for a given period of time, the degree of color development is measured. It is sufficient that the pH of the third reagent solution is properly selected so that the pH of the final color producing solution becomes the optimum pH for coloration of the oxidizable color reagent.

Another process for effectively practicing the process of this invention is to add a predetermined amount of serum to a buffer solution (a first reagent solution) of about pH 7-10 containing, for example, 0.05-20 mmol/liter of xanthine, 0.001-1 mmol/liter of an electron carrier, e.g., 1-methoxy PMS, 2-40 mmol/liter of maleimide or a derivative thereof, e.g., NEM, to heat the solution to 37° C., to add a predetermined amount of a buffer solution (a second reagent solution) of pH 7-10 containing xanthine oxidase so as to make the concentration of xanthine oxidase in the reaction solution 10 to 200 U/liter, 3-40 mmol/liter of citric acid, and/or 0.05-10 ionic milliequivalents/liter of bromine ions, 1-40 mmol/liter of a carbonyl compound and an oxidizable color producing reagent, and $\beta$-(and/or $\gamma$-)cyclodextrin and/or a derivative thereof, and to carry out an enzymic reaction at 37° C. for a predetermined time. Subsequently a predetermined amount of a buffer solution (a third reagent solution) containing a reaction stopper and POD is added to the reaction solution to stop the enzymic reaction and at the same time to begin a color producing reaction between $H_2O_2$ generated and the oxidizable color producing reagent. After the reaction at 37° C. for a predetermined time, the degree of coloring is measured. In this case, the pH of the third reagent solution is also properly selected so that the pH of the final color producing solution becomes the optimum pH for coloration of the oxidizable color reagent.

Selection of either bromine ions, citric acid, or bromine ions and citric acid in addition to the electron carrier, maleimide or a derivative thereof and the carbonyl compound, depends on objects to be measured.

That is, in the case of measuring a sample containing a low concentration of SOD activity, it is suitable to use the process of using bromine ions which are highly sensitive. On the other hand, in the case of measuring a sample containing a high concentration of SOD activity, it is suitable to use the process of using citric acid or a salt thereof, which has a linear calibration curve over a wide range. In such a case, there is no problem caused by the presence of bromine ions.

Further, the process of this invention can be applied to staining of SOD fraction by electrophoresis of protein. As reported by Charles Beauchamp, Irwin Fridovich, et al. (*Anal. Biochem.*, 44, 276–287, 1971), the staining of SOD fraction by electrophoresis of protein utilizes a phenomenon that staining of a support due to reduction of nitro blue tetrazolium by a substrate ($O_2^-$) is inhibited by the presence of SOD, resulting in a decrease of staining in zones of SOD fraction. In this case, it has been difficult to measure the degree of staining by means of a densitometer. However, this invention has opened up the possibility of development of a quantitative staining method.

Moreover, the process of this invention can be expected to be applicable to histochemical staining in a method for observing the localization of SOD activity in tissues or cells by staining.

This invention is further explained in more detail with reference to Examples and Comparative and Referential Examples, which are not by way of limitation but by way of illustration, in which percents are by weight unless otherwise specified.

EXAMPLE 1

Reagents (1) First reagent solution

Xanthine and 1-methoxy PMS were dissolved in 0.1M phosphate buffer (pH 8.0) in concentrations of 3 mmol/liter and 0.03 mmol/liter, respectively.

(2) Second reagent solution

Xanthine oxidase was dissolved in 0.1M phosphate buffer (pH 8.0) in a concentration of 60 U/liter.

(3) Third reagent solution

An aqueous solution containing 35 mmol/liter of sodium dodecyl sulfate, 0.1% of phenol, 0.01% of 4-AAP and 6,000 U/liter of POD was prepared.

Samples

Samples were prepared by dissolving human SOD isolated from human erythrocytes Sigma Chemical Co., (Product Number S7006) in deionized water in concentrations of 5, 10, 15, 20, 40, 60, 80 or 100 U/ml.

Procedure

To 100 μl of each sample was added 1.0 ml of the first reagent solution, and the resulting solution was incubated at 37° C. for 3 minutes, after which 1.0 ml of the second reagent solution was added, and the solution thus obtained was incubated at 37° C. for another 20 minutes. Subsequently, 2.0 ml of the third reagent solution was mixed therewith, and the resulting solution was incubated at 37° C. for 5 minutes. Then, absorbance at a wavelength of 505 nm was measured by using as a control a reagent blank run by repeating the procedure described above, except that deionized water was used in place of the sample. The relationship between SOD activity value and absorbance is shown in FIG. 1. As is obvious from FIG. 1, the calibration curve obtained by plotting the absorbance against the SOD activity value is a straight line passing through the origin and is satisfactorily quantitative. Therefore, in the present process, it is also possible to calculate SOD activity measured values by doing a sum in proportion.

Comparative Example 1

Reagents (1) Color reagent solution I

Xanthine, EDTA.2Na, Triton X-100, β-cyclodextrin, $NO_2$-TB, L-histidine and gelatin were dissolved in 0.1M phosphate buffer (pH 8.0) in concentrations of 0.4 mmol/liter, 0.005%, 0.1%, 0.2%, 0.245 mmol/liter, 10 mmol/liter and 0.3%, respectively.

(2) Color reagent solution II

Xanthine oxidase and EDTA.2Na were dissolved in 0.1M phosphate buffer (pH 8.0) in concentrations of 150 U/liter and 0.005%, respectively.

(3) Enzyme reaction stopper

An aqueous solution containing 0.5% of sodium dodecyl sulfate and 0.3% of gelatin was prepared.

Samples

Samples were prepared by dissolving human SOD mfd. by Sigma Chemical Co. (Product Number S7006) in deionized water in a concentration of 5, 10, 15 or 20 U/ml.

Procedure

To 100 μl of each sample was added 1.0 ml of color reagent solution I, and the resulting solution was incubated at 37° C. for 3 minutes, after which 0.1 ml of color reagent solution II was added, and the solution thus obtained was incubated at 37° C. for 20 minutes. With this solution was mixed 3.0 ml of the enzymic reaction stopper, and absorbance at a wavelength of 560 nm was measured by using reagent blank as control ($E_S$). The reagent blank was run by adding 1.0 ml of color reagent solution I to 0.1 ml of deionized water, incubating the resulting solution at 37° C. for 20 minutes, adding 3.0 ml of the enzymic reaction stopper, and then adding 0.1 ml of color reagent solution II.

Figure 2:
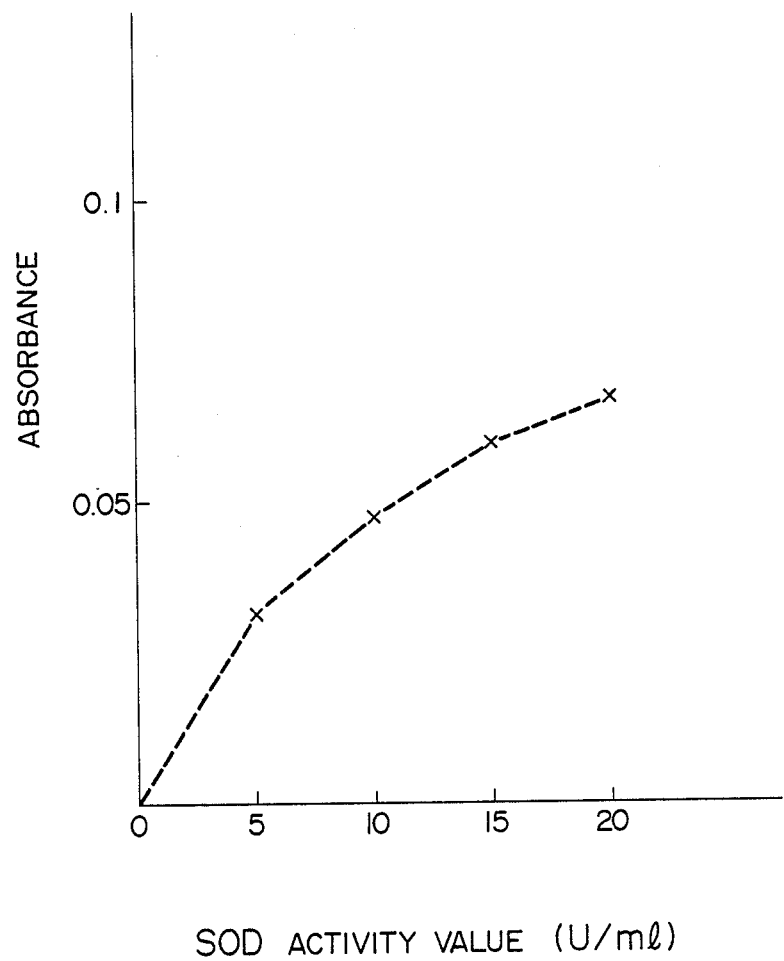
FIG. 2 shows a calibration curve obtained in Comparative Example 1.

The procedure in the case of the sample was repeated, except that 0.1 ml of deionized water was used in place of the sample, and absorbance at a wavelength of 560 nm was measured ($E_B$). The relationship between SOD activity value and absorbance ($E_B$- $E_S$) is shown in FIG. 2. As is obvious from FIG. 2, in this Comparative Example, the calibration curve is non-linear, therefore the precision of determination is low at an SOD activity value of 20 U/ml or more, so that a sample having a high SOD activity should be diluted before measurement, resulting in scatter in measured values.

EXAMPLE 2

Determination of SOD activity in serum (recovery after addition).

As sample solutions, there were used 100 μl each of human serum and solutions prepared by adding SOD to human serum in an amount of 10, 20, 40, 60 or 80 U/ml. In the same manner as in Example 1, each sample was treated and absorbance was measured. The SOD activity value was determined from the calibration curve obtained in Example 1 and the recovery of SOD after addition was calculated. The results obtained are shown in Table 1.

TABLE 1

| Adding amount of SOD (U/ml) | Measured value (U/ml) | Recovery after addition (%) |
| --- | --- | --- |
| 0 | 12.5 | — |
| 10 | 22.7 | 101 |
| 20 | 32.2 | 99.0 |
| 40 | 53.0 | 101 |
| 60 | 72.1 | 99.4 |
| 80 | 91.8 | 99.2 |

EXAMPLE 3

Determination of SOD activity in serum (recovery after addition).

As sample solutions, serum samples having an SOD activity value of 5.0 to 32.0 U/ml were used. To each sample solution was added 20 U/ml or 40 U/ml of SOD. In the same manner as in Example 1, the resulting solution was treated and absorbance was measured. The SOD activity value was determined from the calibration curve obtained in Example 1 and the recovery of SOD after addition was calculated. The results obtained are shown in Table 2.

TABLE 2

| Adding amount of SOD (U/ml) | Recovery of SOD (%) |
| --- | --- |
| 20 | av. 99.28 (n = 10) |
| 40 | av. 99.42 (n = 10) |

EXAMPLE 4

Reagents (1) First reagent solution

Xanthine, 1-methoxy PMS, NEM and HMBP were dissolved in 0.05M Tris-HCl buffer (pH 7.85) in concentrations of 0.3 mmol/liter, 0.03 mmol/liter, 8 mmol/liter and 5 mmol/liter, respectively.

(2) Second reagent solution

Xanthine oxidase was dissolved in 0.05M Tris-HCl buffer (pH 7.85) in a concentration of 60 U/liter.

(3) Third reagent solution

Sodium dodecyl sulfate, N-ethyl-N-(2-hydroxy-3-sulfopropyl)-m-toluidine sodium (hereinafter abbreviated to TOOS), 4-AAP and POD were dissolved in 0.05M phosphate buffer (pH 7.0) in concentrations of 70 mmol/liter, 0.1%, 0.01% and 5,000 U/liter, respectively.

Samples

Samples were prepared by dissolving human erythrocyte SOD mfd. by Sigma Chemical Co. (Product Number S7006) in a concentration of 5, 10, 15, 20, 40, 60, 80 or 100 U/ml.

Procedure

Figure 3:
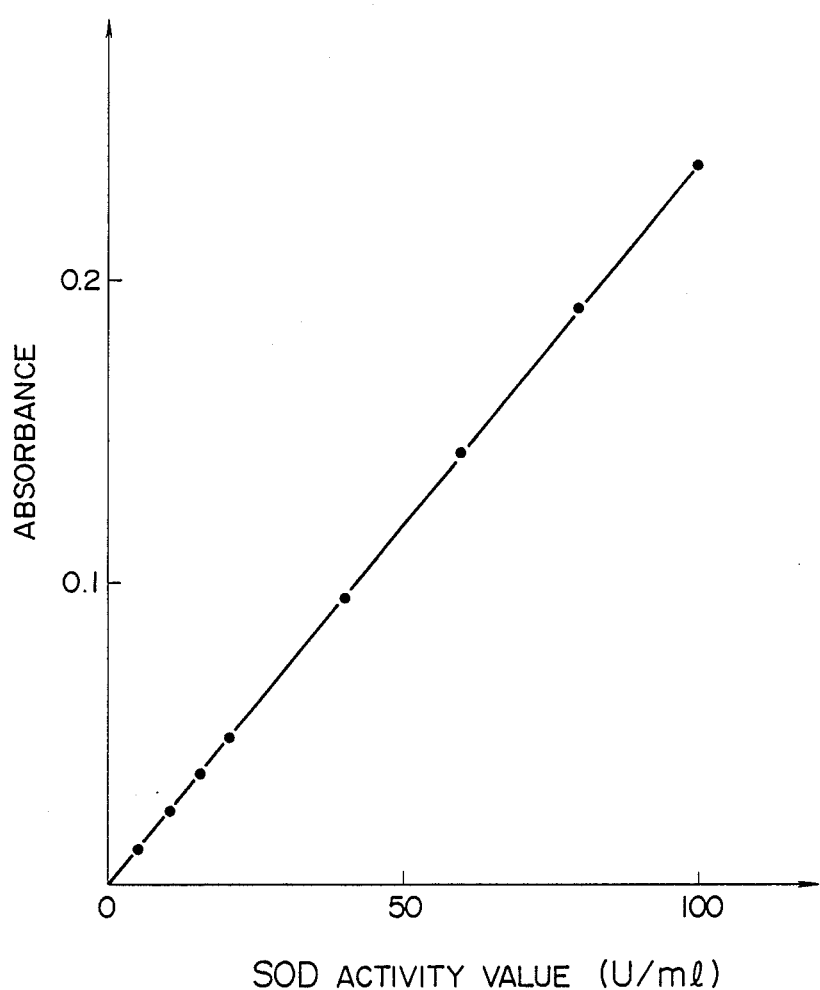
FIG. 3 shows a calibration curve obtained in Example 4.

To 50 μl of each sample was added 1.0 ml of the first reagent solution and the resulting solution was incubated at 37° C. for 3 minutes, after which 1.0 ml of the second reagent solution was added, and the solution thus obtained was incubated at 37° C. for another 20 minutes. Subsequently, 2.0 ml of the third reagent solution was mixed therewith, and the resulting solution was incubated at 37° C. for 5 minutes. Then, absorbance at a wavelength of 555 nm was measured by using as control a reagent blank run by repeating the procedure described above, except that deionized water was used in place of the sample. Separately, the absorbance of the reagent blank was measured by using deionized water as control. The relationship between SOD activity value and absorbance is shown in FIG. 3. As is obvious from FIG. 3, the calibration curve obtained by plotting the absorbance against the SOD activity value is a straight line passing through the origin and is satifactorily quantitative.

EXAMPLE 5

Reagents (1) First reagent solution

There was prepared a reagent solution having the same composition as that of the first reagent solution in Example 4, except that HMBP was omitted.

(2) Second reagent solution

The same as in Example 4.

(3) Third reagent solution

The same as in Example 4.

Sample

A sample was prepared by dissolving human erythrocyte SOD mfd. by Sigma Chemical Co. in deionozed water in a concentration of 40 U/ml.

Procedure

The same as in Example 4.

Referential Example 1

Reagents (1) First reagent solution

There was prepared a reagent solution having the same composition as that of the first reagent solution in Example 4, except that NEM and HMBP were omitted.

(2) Second reagent solution

The same as in Example 4.

(3) Third reagent solution

The same as in Example 4.

Sample

The same as in Example 5.

Procedure

The same as in Example 4.

Referential Example 2

Reagents (1) First reagent solution

There was prepared a reagent solution having the same composition as that of the first reagent solution in Example 4, except that NEM was omitted.

(2) Second reagent solution

The same as in Example 4.

(3) Third reagent solution

The same as in Example 4.

Sample

The same as in Example 5.

Procedure

The same as in Example 4.

In Table 3 are shown the absorbances of reagent blank and the absorbances of sample (containing 40 U/ml of SOD) in Example 4, Example 5, Referential Example 1 and Referential Example 2.

TABLE 3

| | Example 4 | Example 5 | Referential Example 1 | Referential Example 2 |
| --- | --- | --- | --- | --- |
| Absorbance of reagent blank | 0.48 | 0.153 | 0.190 | 0.041 |
| Absorbance | 0.094 | 0.114 | 0.112 | 0.059 |

TABLE 3-continued

| | Example 4 | Example 5 | Referential Example 1 | Referential Example 2 |
|---|---|---|---|---|
| of sample | | | | |

Note: The absorbances of reagent blank were measured by using deionized water as control and the absorbances of samples were measured by using the respective reagent blanks as controls.

As is evident from Table 3, the absorbance of reagent blank in Example 5 in which NEM was used is about four-fifths as high as that in Referential Example 1 in which no NEM was used. In Example 4 in which NEM and HMBP were simultaneously used, the absorbance of reagent blank is one-fourth as high as that in Referential Example 1. Thus, a marked effect was brought about.

On the other hand, in Referential Example 2 in which HMBP alone, but no NEM, was used, the absorbance of reagent blank is substantially the same as in Example 4 in which NEM and HMBP were simultaneously used, but concomitantly, the absorbance of sample also has a small value and the sensitivity is low.

EXAMPLE 6

Reagents
(1) First reagent solution

Xanthine, 1-methoxy PMS, NEM and HMBP were dissolved in 0.1M phosphate buffer (pH 8.0) in concentrations of 3 mmol/liter, 0.03 mmol/liter, 8 mmol/liter and 5 mmol/liter, respectively.

(2) Second reagent solution

Xanthine oxidase was dissolved in 0.1M phosphate buffer (pH 8.0) in a concentration of 60 U/liter.

(3) Third reagent solution

There was prepared an aqueous solution containing 35 mmol/liter of sodium dodecyl sulfate, 0.1% of phenol, 0.01% of 4-AAP and 6,000 U/liter of POD.

Samples

The same as in Example 4.

Procedure

In the same manner as in Example 4, 100 μl of each sample was treated and absorbance at a wavelength of 505 nm was measured.

Separately, the absorbance of reagent blank was measured by using deionized water as control.

Figure 4:
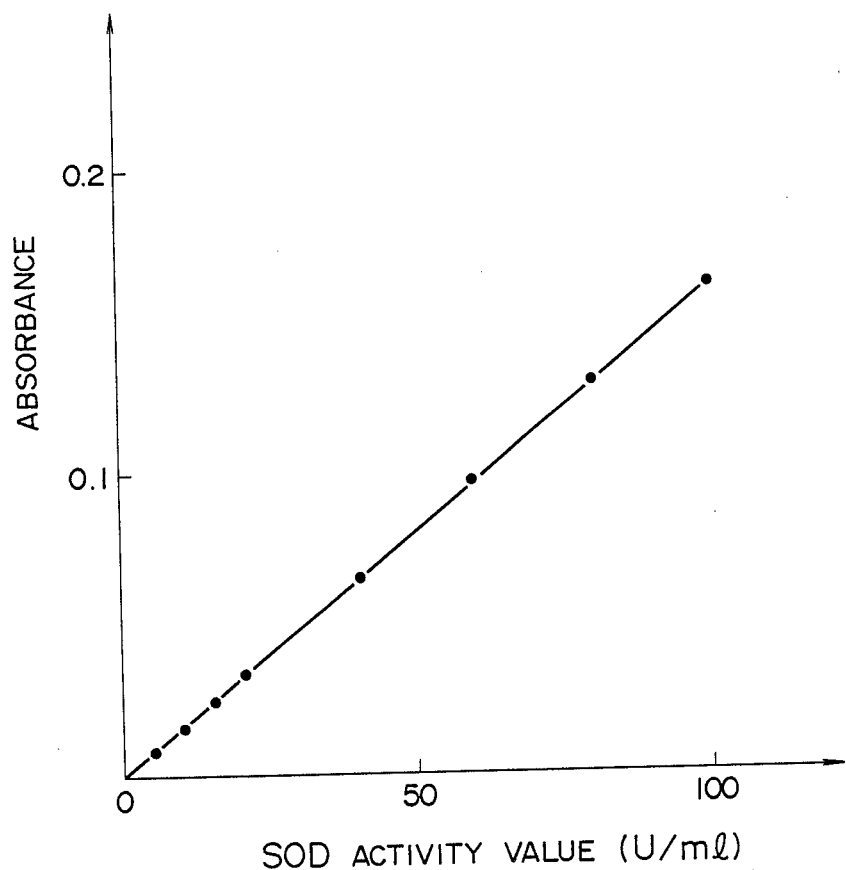
FIG. 4 shows a calibration curve obtained in Example 6.

The relationship between SOD activity value and absorbance is shown in FIG. 4. As is obvious from FIG. 4, the calibration curve obtained by plotting the absorbance against the SOD activity value is a straight line passing through the origin and is satisfactorily quantitative.

EXAMPLE 7

Reagents
(1) First reagent solution

There was prepared a reagent solution having the same composition as that of the first reagent solution in Example 6, except that HMBP was omitted.

(2) Second reagent solution
The same as in Example 6.
(3) Third reagent solution
The same as in Example 6.
Sample
A sample was prepared by dissolving human erythrocyte SOD mfd. by Sigma Chemical Co. in deionized water in a concentration of 40 U/ml.
Procedure
The same as in Example 6.

Referential Example 3
Reagents
(1) First reagent solution

There was prepared a reagent solution having the same composition as that of the first reagent solution in Example 6, except that NEM and HMBP were omitted.

(2) Second reagent solution
The same as in Example 6.
(3) Third reagent solution
The same as in Example 6.
Samples
The same as in Example 7.
Procedure
The same as in Example 6.

Referential Example 4
Reagents
(1) First reagent solution

There was prepared a reagent solution having the same composition as that of the first reagent solution in Example 6, except that NEM was omitted.

(2) Second reagent solution
The same as in Example 6.
(3) Third reagent solution
The same as in Example 6.
Sample
The same as in Example 7.
Procedure
The same as in Example 6.

In Table 4 are shown the absorbances of reagent blank and the absorbances of samples (containing 40 U/ml of SOD) in Example 6, Example 7, Referential Example 3 and Referential Example 4.

TABLE 4

| | Example 6 | Example 7 | Referential Example 3 | Referential Example 4 |
|---|---|---|---|---|
| Absorbance of reagent blank | 0.020 | 0.040 | 0.057 | 0.021 |
| Absorbance of sample | 0.064 | 0.071 | 0.069 | 0.030 |

Note: The absorbances of reagent blank were measured by using deionized water as control and the absorbances of samples were measured by using the respective reagent blanks as controls.

As is evident from Table 4, the value of the absorbance of reagent blank in Example 7 in which NEM was used is about 30% lower than that in Referential Example 3 in which no NEM was used. In Example 6 in which NEM and HMBP were simultaneously used, the value of the absorbance of reagent blank is about one-third as high as that in Referential Example 3: thus, a more marked effect was brought about.

On the other hand, in Referential Example 4 in which HMBP alone, but no NEM, was used, the absorbance of reagent blank is substantially the same as in Example 6 in which NEM and HMBP were simultaneously used, but concomitantly, the absorbance of sample also has a small value and the sensitivity is low.

EXAMPLE 8

The procedure in Example 6 was repeated, except that maleimide was used in place of NEM, to obtain the same results as in Example 6.

EXAMPLE 9

Reagents
(1) First reagent solution

Xanthine, 1-methoxy PMS, NEM and HMBP were dissolved in 0.05M phosphate buffer (pH 8.0) in concentrations of 0.3 mmol/liter, 0.03 mmol/liter, 8 mmol/liter and 5 mmol/liter, respectively.

(2) Second reagent solution

Xanthine oxidase, 4-AAP and TODS were dissolved in 0.05M phosphate buffer (pH 8.0) in concentrations of 60 U/liter, 0.01% and 0.1%, respectively.

(3) Third reagent solution

Sodium dodecyl sulfate and POD were dissolved in 0.2M sodium dihydrogenphosphate solution in concentrations of 70 mmol/liter and 5,000 U/liter, respectively.

Samples

Samples were prepared by dissolving human erythrocyte SOD mfd. by Sigma Chemical Co. (Product Number S7006) in deionized water in a concentration of 5, 10, 15, 20, 40, 60, 80 or 100 U/liter.

Procedure

To 100 μl of each sample was added 1.0 ml of the first reagent solution, and the resulting solution was incubated at 37° C. for 3 minutes, after which 1.0 ml of the second reagent solution was added, and the solution thus obtained was incubated at 37° C. for another 20 minutes. Subsequently, 2.0 ml of the third reagent solution was mixed therewith, and the resulting solution was incubated at 37° C. for 5 minutes. Then absorbance at a wavelength of 555 nm was measured by using as control a reagent blank run by repeating the procedure described above, except that deionozed water was used in place of the sample.

Figure 5:
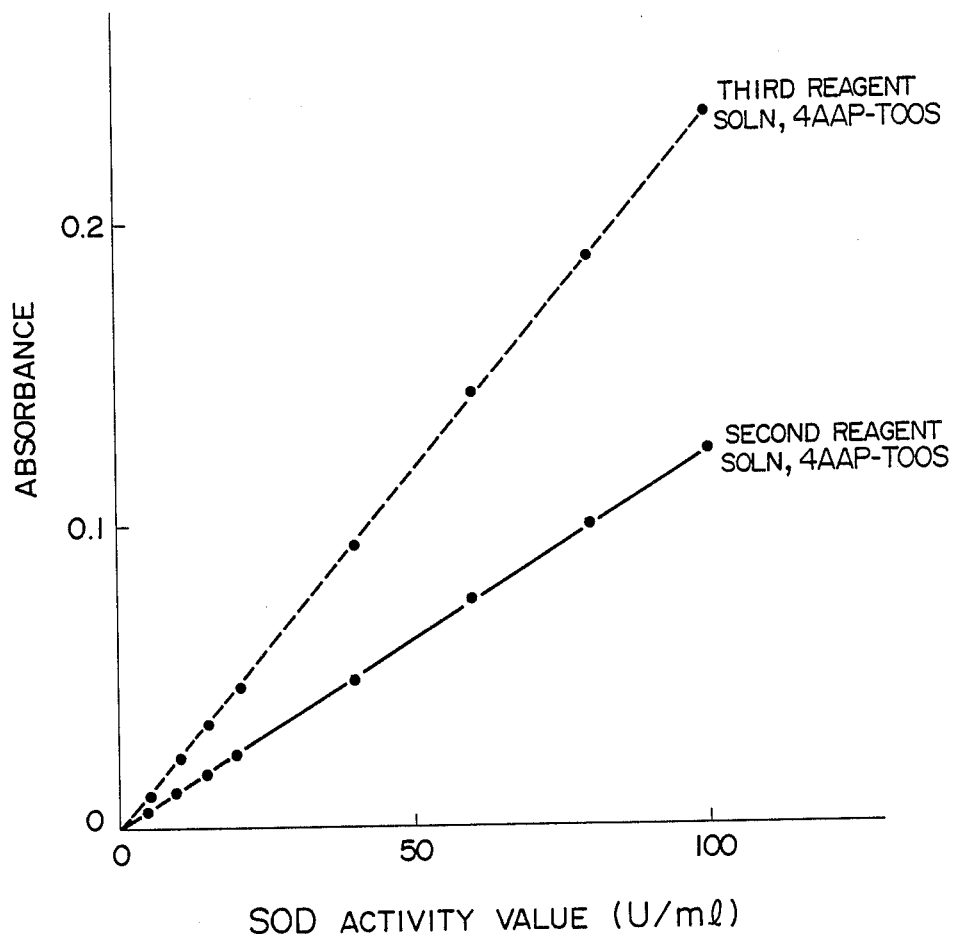
FIG. 5 shows a calibration curve obtained in Example 9.

The relationship between SOD activity value and absorbance is shown in FIG. 5. As is obvious from FIG. 5, the calibration curve obtained by plotting the abosrbance against the SOD activity is a straight line passing through the origin and is satisfactorily quantitative. However, this calibration curve has a slope gentler than that of the calibration curve (shown by the dotted line) obtained when 4-AAP and TOOS were omitted from the second reagent solution and incorporated into the third reagent solution, indicating that in the case of the former calibration curve, the absorbance at the same SOD activity is lower than in the case of the latter. This suggests that the color reagents used have some influence on the enzymic reaction system.

EXAMPLE 10

Reagents (1) First reagent solution

Xanthine, 1-methoxy PMS and NEM were dissolved in 0.05M phosphate buffer (pH 8.0) in concentrations of 0.3 mmol/liter, 0.03 mmol/liter and 8 mmol/liter, respectively.

(2) Second reagent solution

Xanthine oxidase, 4-AAP, N-ethyl-N-(2-hydroxy-3-sulfopropyl)aniline (ALOS) and HMBP were dissolved in 0.05M phosphate buffer (pH 8.0) in concentrations of 60 U/liter, 0.01%, 0.1% and 5 mmol/liter, respectively.

(3) Third reagent solution

Sodium dodecyl sulfate and POD were dissolved in 0.2M sodium dihydrogenphosphate solution in concentrations of 70 mmol/liter and 5,000 U/liter, respectively.

Samples

Samples were prepared by dissolving human erythrocyte SOD mfd. by Sigma Chemical Co. (Product Number S7006) in deionized water in a concentration of 5, 10, 15, 20, 40, 60, 80 or 100 U/ml.

Procedure

To 100 μl of each sample was added 1.0 ml of the first reagent solution, and the resulting solution was incubated at 37° C. for 3 minutes, after which 1.0 ml of the second reagent solution was added, and the solution thus obtained was incubated at 37° C. for another 20 minutes. Subsequently, 2.0 ml of the third reagent solution was mixed therewith, and the resulting solution was incubated at 37° C. for 5 minutes. Then, absorbance at a wavelength of 565 nm was measured by using as control a reagent blank run by repeating the procedure described above, except that deionized water was used in place of the sample.

Figure 6:
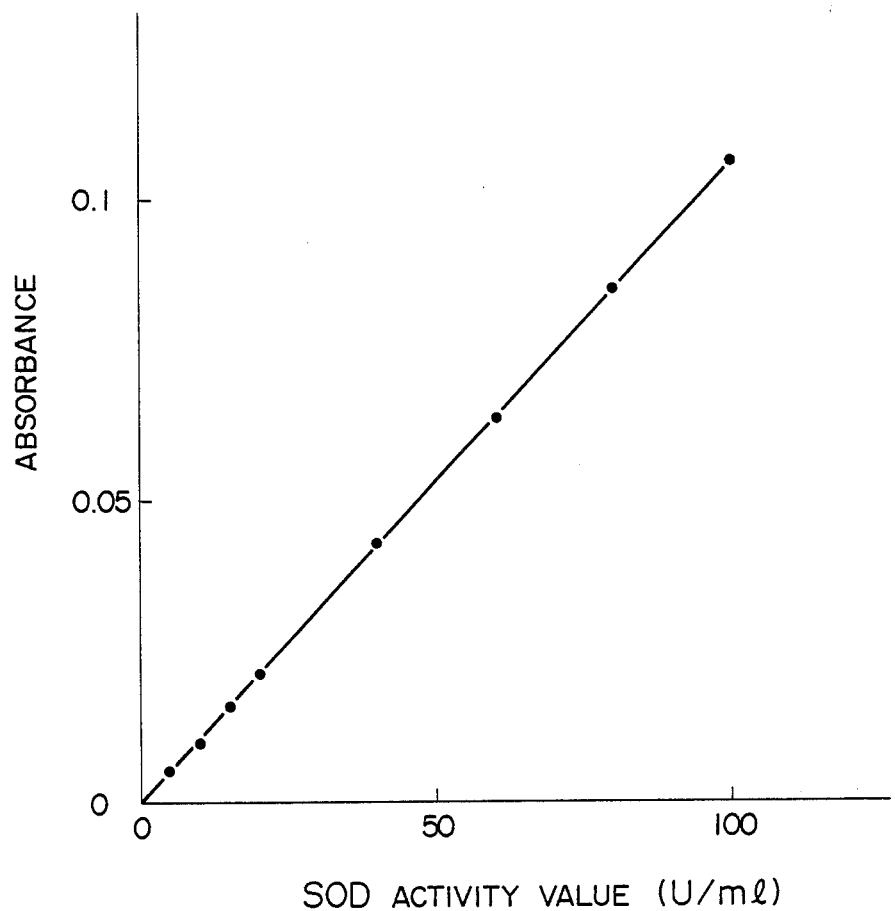
FIG. 6 shows a calibration curve obtained in Example 10.

The relationship between SOD activity value and absorbance is shown in FIG. 6. As is obvious from FIG. 6, the calibration curve obtained by plotting the absorbance against the SOD activity value is a straight line passing through the origin and is satisfactorily quantitative.

EXAMPLE 11

Reagents (1) First reagent solution

Xanthine, 1-methoxy PMS, sodium bromide, NEM and HMBP were dissolved in 0.05M phosphate buffer (pH 8.0) in concentrations of 0.3 mmol/liter, 0.03 mmol/liter, 7 mmol/liter, 8 mmol/liter and 5 mmol/liter, respectively.

(2) Second reagent solution

Xanthine oxidase was dissolved in 0.05M phosphate buffer (pH 8.0) in a concentration of 60 U/liter.

(3) Third reagent solution

Sodium dodecyl sulfate, TODS, 4-AAP and POD were dissolved in 0.2M sodium dihydrogenphosphate solution in concentrations of 70 mmol/liter, 0.2%, 0.02% and 5,000 U/liter, respectively.

Samples

Samples were prepared by dissolving human erythrocyte SOD mfd. by Sigma Chemical Co. (Product Number S7006) in deionized water in a concentration of 50, 100 or 150 U/ml.

Procedure

To 100 μl of each sample was added 1.0 ml of the first reagent solution, and the resulting solution was incubated at 37° C. for 3 minutes, after which 1.0 ml of the second reagent solution was added, and the solution thus obtained was incubated at 37° C. for another 20 minutes. Subsequently, 2.0 ml of the third reagent solution was mixed therewith, and the resulting solution was incubated at 37° C. for 5 minutes. Then, absorbance at a wavelength of 555 nm was measured by using as control a reagent blank run by repeating the procedure described above, except that deionized water was used in place of the sample. Separately, the absorbance of the reagent blank was measured by using deionized water as control.

The relationship between SOD activity value and absorbance is shown in FIG. 7. As is obvious from FIG. 7, the calibration curve obtained by plotting the absorbance against the SOD activity value passed through the origin and was linear up to an SOD activity value of 150 U/ml.

Referential Example 5

Reagents (1) First reagent solution

There was prepared a reagent solution having the same composition as that of the first reagent solution in Example 11, except that sodium bromide was omitted.

(2) Second reagent solution
The same as the second solution in Example 11.
(3) Third reagent solution
The same as the third reagent solution in Example 11.
Samples
The same as in Example 11.
Procedure
The same as in Example 11.

Figure 8:
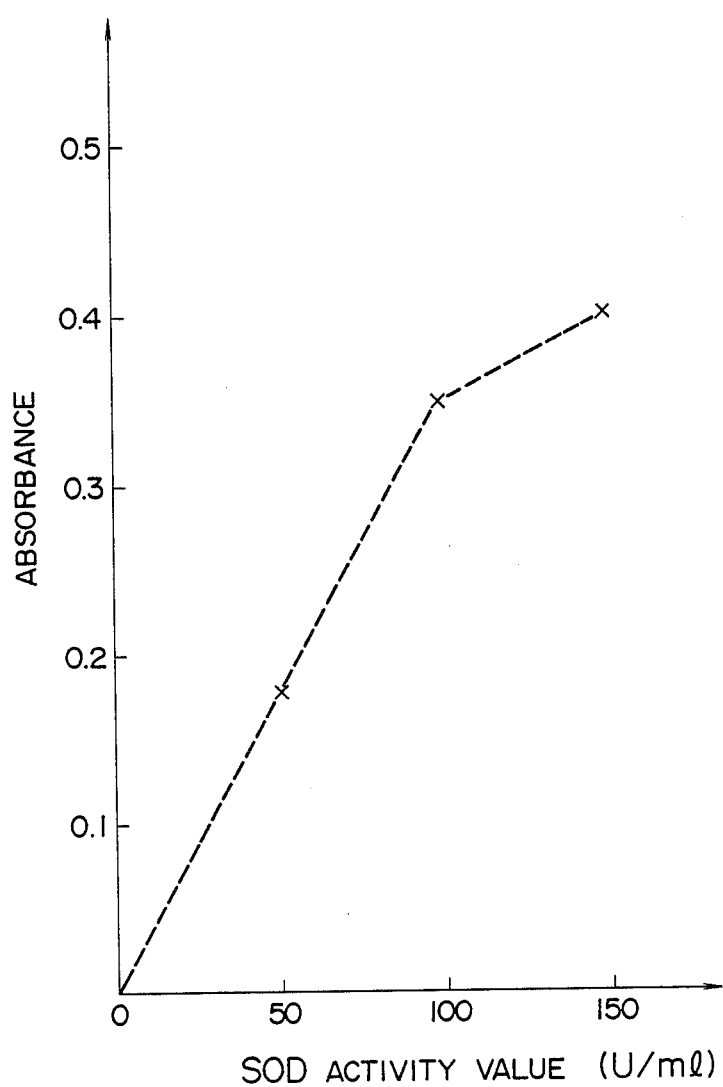
FIG. 8 shows a calibration curve obtained in Referential Example 5.

In Table 5 are shown the absorbances of reagent blank and the absorbances of samples (containing 150 U/liter of SOD) in Example 11 and Referential Example 5. A calibration curve obtained in Referential Example 5 is shown in FIG. 8.

TABLE 5

|  | Example 11 | Referential Example 5 |
|---|---|---|
| Absorbance of reagent blank | 0.018 | 0.020 |
| Absorbance of sample | 0.485 | 0.400 |

Note: The absorbances of reagent blank were measured by using deionized water as control and the absorbances of samples were measured by using the respective reagent blanks as controls.

As is evident from Table 5, there is no significant difference in absorbance of reagent blank between Example 11 and Referential Example 5, but there is a marked difference between them in absorbance of sample. As shown in FIG. 7, the calibration curve obtained in Example 11 is linear up to an SOD activity of 150 U/ml, but in Referential Example 5, as shown in FIG. 8, the absorbance at an SOD activity value of 150 U/ml is considerably outside the linearity region.

EXAMPLE 12

Reagents
(1) First reagent solution
A reagent solution was prepared in the same manner as with the first reagent solution in Example 11, except that 2.75 mmol/liter of cetyl trimethylammonium bromide was used in place of 7 mmol/liter of sodium bromide.
(2) Second reagent solution
The same as the second reagent solution in Example 11.
(3) Third reagent solution
The same as the third reagent solution in Example 11.
Samples
The same as in Example 11.
Procedure
The same as in Example 11.

Figure 9:
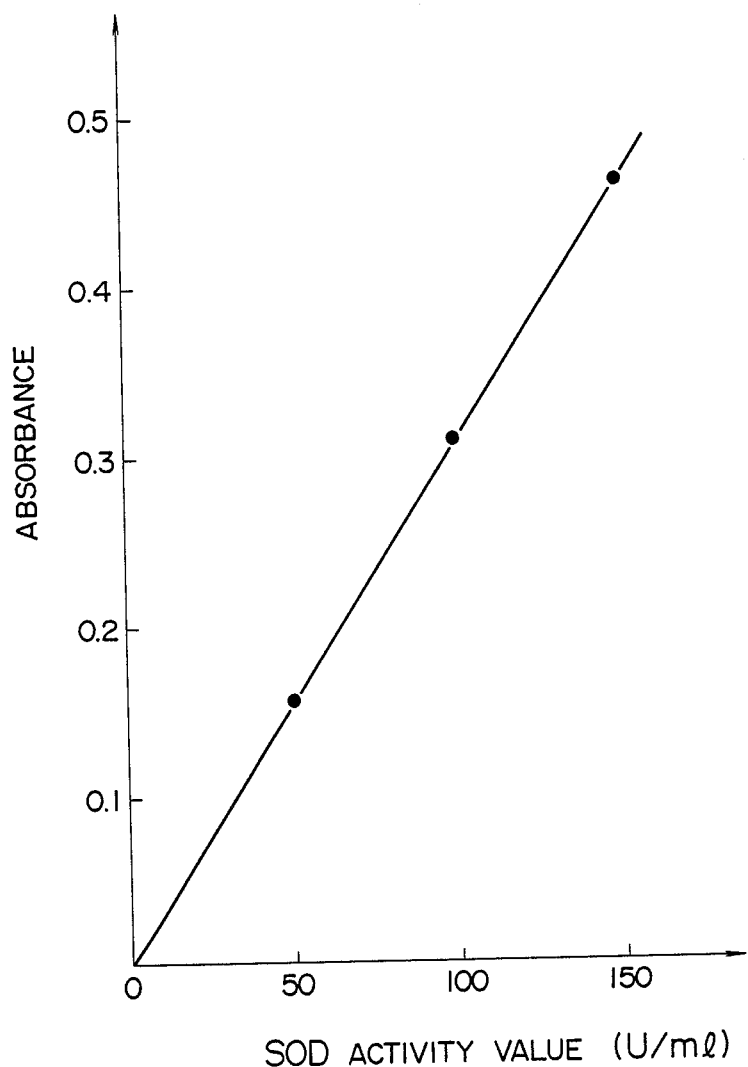
FIG. 9 shows a calibration curve obtained in Example 12.

The relationship between SOD activity value and absorbance in this Example is shown in FIG. 9. As is obvious from FIG. 9, the calibration curve obtained by plotting the absorbance against the SOD activity value passed through the origin and was linear up to an SOD activity value of 150 U/ml.

EXAMPLE 13

Reagents
(1) First reagent solution
A reagent solution was prepared in the same manner as with the first reagent solution in Example 12, except that 5 mmol/liter of tetramethylammonium bromide was used in place of 2.75 mmol/liter of cetyl trimethylammonium bromide.
(2) Second reagent solution
The same as the second reagent solution in Example 11.
(3) Third reagent solution
The same as the third reagent solution in Example 11.
Samples
The same as in Example 11.
Procedure
The same as in Example 11.

Referential Examples 6 and 7
SOD activity values were measured and calibration curves were obtained in exactly the same manner as in Example 13, except that there was used a first reagent solution prepared in the same manner as with the first reagent solution in Example 13 except for replacement of tetramethylammonium bromide by tetramethylammonium chloride (Referential Example 6) or tetramethylammonium iodide (Referential Example 7).

Figure 10:
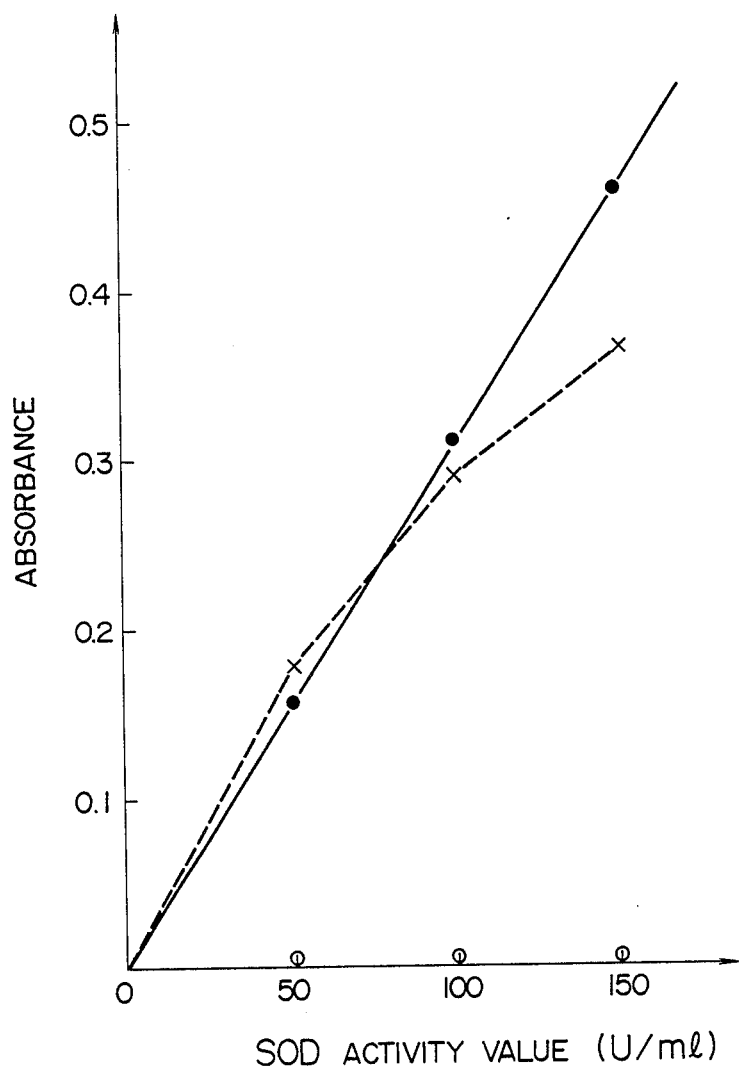
FIG. 10 shows calibration curves obtained in Example 13 and Referential Example 6 and measurement results obtained in Referential Example 7 (- • - shows the calibration curve obtained in Example 13, -- X -- the calibration curve obtained in Referential Example 6, and O the measurement results obtained in Referential Example 7).

The calibration curves obtained in Example 13 and Referential Examples 6 and 7 are shown in FIG. 10, in which the calibration curve obtained in Example 13 is shown by -●-, the calibration curve obtained in Referential Example 6 is shown by -- X --, and the measurement result obtained in Referential Example 7 is shown by O. As is obvious from FIG. 10, in Example 13, the calibration curve obtained by plotting the absorbance against the SOD activity value was a straight line passing through the origin up to an SOD activity value of 150 U/ml. However, in Referential Example 6, the calibration curve had different slopes at SOD activity values of 0 to 50 U/ml, 50 to 100 U/ml and 100 to 150 U/ml and was thus insufficiently quantitative. In Referential Example 7, no coloration occurred at all at any SOD activity value and measurement was impossible.

EXAMPLE 14

Reagents
(1) First reagent solution
Xanthine, 1-methoxy PMS and NEM were dissolved in 0.05 phosphate buffer (pH 8.0) in concentrations of 0.3 mmol/liter, 0.03 mmol/liter and 8 mmol/liter, respectively.
(2) Second reagent solution
Xanthine oxidase, 4-AAP, TOOS, trisodium citrate dihydrate and HMBP were dissolved in 0.05M phosphate buffer (pH 8.0) in concentrations of 60 U/liter, 0.01%, 0.1%, 17 mmol/liter and 5 mmol/liter, respectively.
(3) Third reagent solution
Sodium dodecyl sulfate and POD were dissolved in 0.2M sodium dihydrogenphosphate solution in concentration of 70 mmol/liter and 5,000 U/liter, respectively.
Samples
Samples were prepared by dissolving human erythrocyte SOD mfd. by Sigma Chemical Co. (Product Number S7006) in deionized water in a concentration of 50, 100, 150 or 200 U/ml.
Procedure
To 100 ml of each sample was added 1.0 ml of the first reagent solution, and the resulting solution was incubated at 37° C. for 3 minutes, after which 1.0 ml of the second reagent solution was added, and the solution thus obtained was incubated at 37° C. for another 20 minutes. Subsequently, 2.0 ml of the third reagent solution was mixed therewith, and the resulting solution was incubated at 37° C. for 5 minutes. Then, absorbance at a wavelength of 555 nm was measured by using as control a reagent blank run by repeating the procedure described above, except that deionized water was used in place of the sample.

Referential Example 8

Reagents (1) First reagent solution

The same as the first reagent solution in Example 14.

(2) Second reagent solution

A second reagent solution was prepared in the same manner as described in Example 14 except for not using trisodium citrate.

(3) Third reagent solution

The same as the third reagent solution in Example 14.

Samples

The same as in Example 14.

Procedure

The same as in Example 14.

Figure 11:
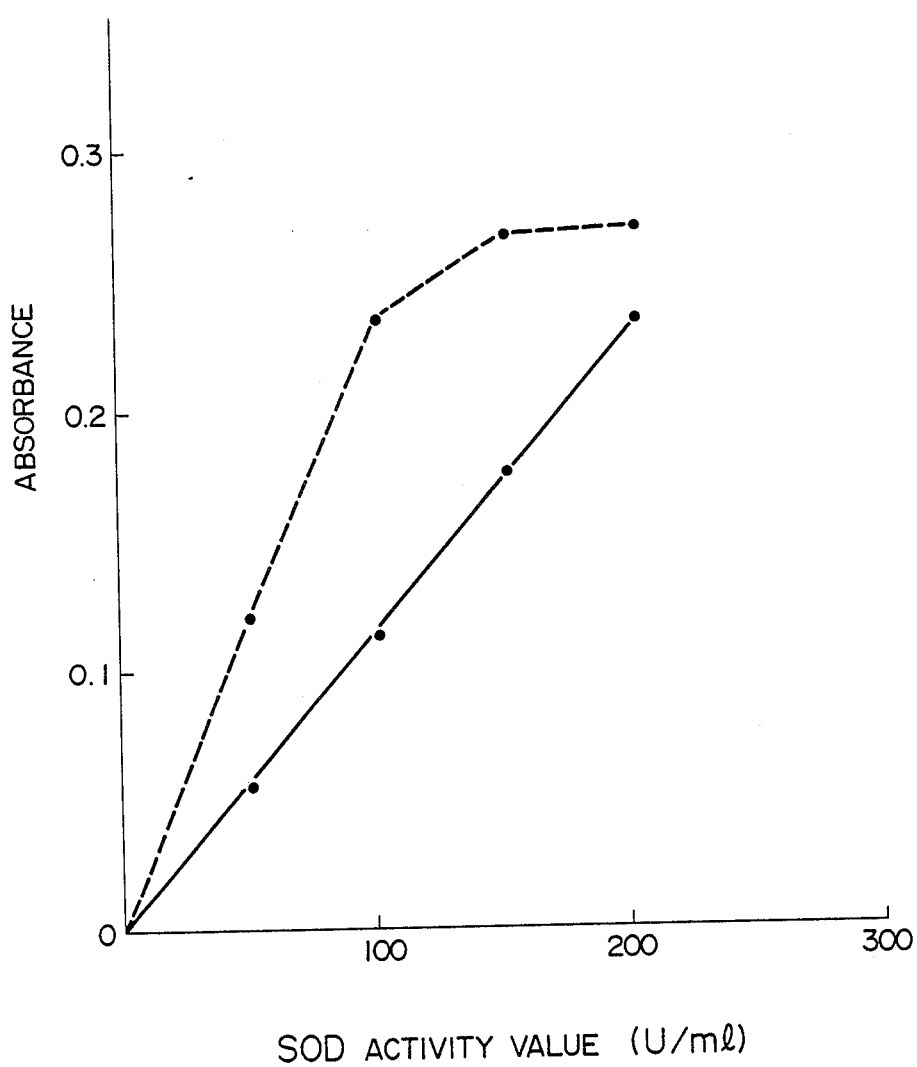
FIG. 11 shows calibration curves obtained in Example 14 (- • -) and Referential Example 8 (--- • ---).

Calibration curves obtained in Example 14 and Referential Example 8 are shown in FIG. 11, wherein the curve -●- shows Example 14 and the curve --- ● --- shows Referential Example 8.

As is clear from FIG. 11, the calibration curve of Example 14 is a linear line started from the zero point until the SOD activity value reaches 200 U/ml, whereas the calibration curve of Referential Example 8 curves beyond the SOD activity value of 100 U/ml and becomes unacceptable for quantitation.

Referential Examples 9 to 17

Reagents (1) First reagent solution

The same as the first reagent solution in Example 14.

(2) Second reagent solution

A second reagent solution was prepared in the same manner as described in Example 14 except for using 17 mmol/liter of various organic acids or salts thereof as shown in Table 6 (lactic acid, glycolic acid, malic acid, disodium tartarate dihydrate, succinic acid, sodium acetate, sodium benzoate, maleic acid, malonic acid) in place of 17 mmol/liter of trisodium citrate dihydrate.

(3) Third reagent solution

The same as the third reagent solution in Example 14.

Samples

The same as in Example 14.

Procedure

The same as in Example 14.

The results obtained in Example 14 and Referential Examples 9 to 17 are shown in Table 6.

methoxy PMS, 7 mmol/liter of sodium bromide and 8 mmol/liter of NEM in 0.05M phosphate buffer (pH 8.0).

(2) Second reagent solution

The same as the second reagent solution in Example 14.

(3) Third reagent solution

The same as the third reagent solution in Example 14.

Samples

The same as in Example 14.

Procedure

The same as in Example 14.

Figure 12:
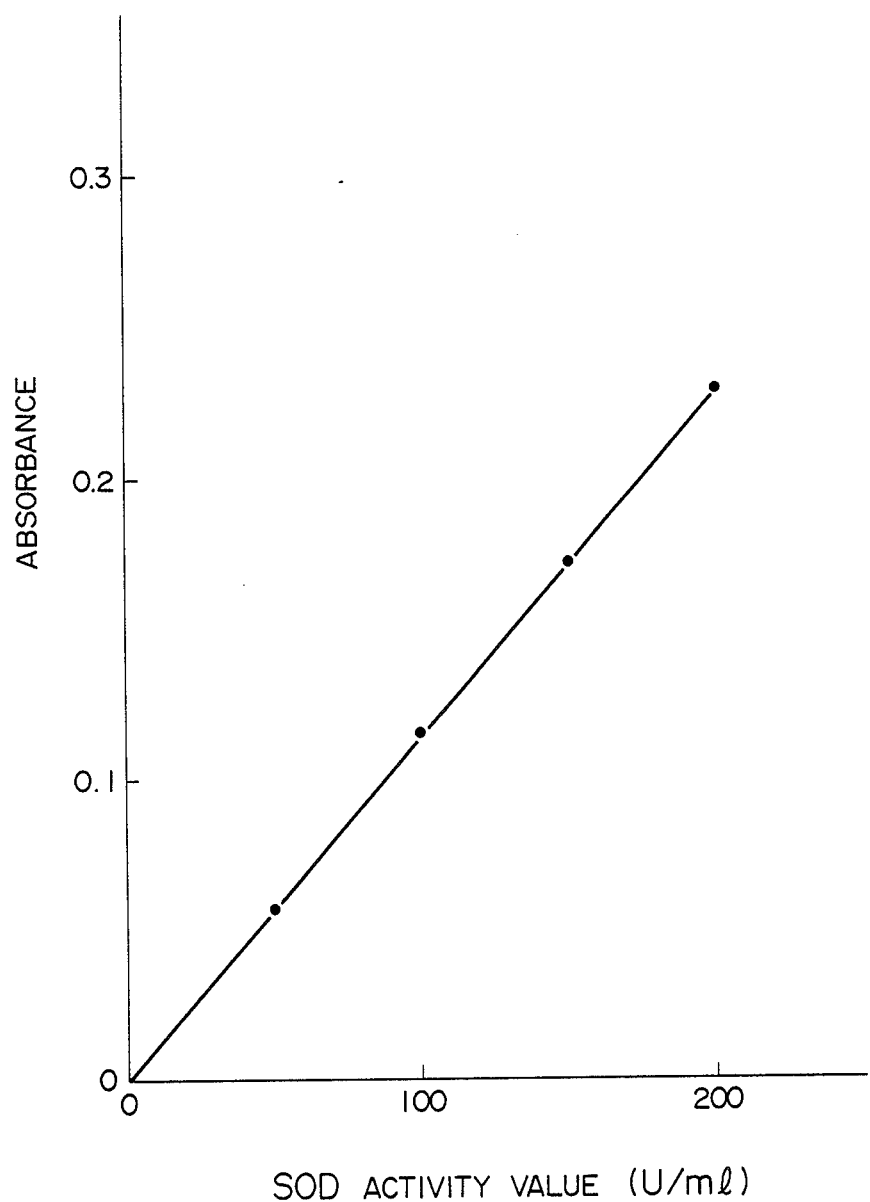
FIG. 12 shows a calibration curve obtained in Example 15. All the calibration curves were obtained by plotting absorbance as ordinate against SOD activity value (U/ml) as abscissa.

FIG. 12 shows a relation between the SOD activity value (U/ml) and the absorbance. As is clear from FIG. 12, the calibration curve obtaind by lining plotted absorbances corresponding to individual SOD activity values becomes a linear line starting from the zero point until the value of 200 U/ml and shows good quantitativeness.

As described above in detail, this invention provides a process for determining SOD activity contained in body fluids, e.g., serum and the like by determining $H_2O_2$ produced from $O_2^-$ by the action of SOD in the presence of an electron carrier, and brings about marked effects in that improvements are made in low precision of determination due to high reagent blank value, narrow range of determination, and the like which are defects of conventional processes. Further, this invention brings about marked effects in that in the process for determining SOD activity by determining $H_2O_2$ produced from $O_2^-$ by the action of SOD in the presence of an electron carrier, reagent blank value and its variation are reduced by the presence of maleimide or a maleimide derivative and a carbonyl compound in the system so as to be prevented from affecting measured values. Moreover, this invention provides a process for determining SOD activity by determining $H_2O_2$ produced from $O_2^-$ by the action of SOD in the presence of an electron transporter, maleimide or a derivative thereof, a carbonyl compound and bromine ion, or citric acid or a salt thereof. By the latter process, the sensitivity increases, the linearity of calibration curve is improved and the detection range is more broadened by the use of bromine ions in the measuring system, while the detection range is more broadened by the use of citric acid or a salt thereof in the measuring

TABLE 1

| SOD concentration | No addition | Organic acid or salt thereof | | | | | | | | | |
|---|---|---|---|---|---|---|---|---|---|---|---|
| | | Trisodium citrate dihydrate | Lactic acid | Glycolic acid | Malic acid | Disodium tartarate dihydrate | Succinic acid | Sodium acetate | Sodium benzoate | Maleic acid | Malonic acid |
| 50 (U/ml) | 0.161 | 0.054 | 0.148 | 0.156 | 0.063 | 0.152 | 0.156 | 0.168 | 0.167 | 0.152 | 0.153 |
| 100 | 0.235 | 0.119 | 0.223 | 0.231 | 0.072 | 0.216 | 0.217 | 0.241 | 0.238 | 0.209 | 0.212 |
| 150 | 0.267 | 0.174 | 0.253 | 0.252 | 0.084 | 0.248 | 0.251 | 0.272 | 0.269 | 0.242 | 0.249 |
| 200 | 0.270 | 0.231 | 0.259 | 0.257 | 0.092 | 0.262 | 0.269 | 0.279 | 0.280 | 0.260 | 0.262 |
| Reagent blank (control: water) | 0.030 | 0.036 | 0.024 | 0.025 | 0.024 | 0.035 | 0.054 | 0.025 | 0.050 | 0.025 | 0.025 |

As is evident from Table 6, the results obtained by addition of the organic acids other than citric acid were hardly different from those obtained without addition thereof, and no effect like the effect of citric acid was obtained at all.

EXAMPLE 15

Reagents (1) First reagent solution

A first reagent solution was prepared by dissolving 0.3 mmol/liter of xanthine, 0.03 mmol/liter of 1- system.

What is claimed is:

1. A process for determining superoxide dismutase activity which comprises (i) producing superoxide anions by a method selected from the group consisting of (a) the reaction of xanthine with xanthine oxidase, (b) the use of a superoxidized compound, and (c) the reaction of a reduced form coenzyme with an electron carrier, (ii) reacting superoxide dismutase with the superoxide anions produced in step (i) in the presence of an electron carrier to produce hydrogen peroxide, and (iii) determining the amount of hydrogen peroxide produced thereform colorimetrically wherein the amount of hydrogen peroxide produced is an indication of superoxide dismutase activity present.

2. A process according to claim 1, wherein the electron carrier is at least one member selected from the group consisting of phenazine methosulfate, 1-methoxy-5-methylphenazinium methylsulfate, and 9-dimethylaminobenzo-α-phenazoxonium chloride.

3. A process according to claim 1, wherein the determination of hydrogen peroxide is carried out colorimetrically by using a peroxidase and a color reagent after stopping the enzymic reaction or at the time of stopping the enzymic reaction by using an enzymic reaction stopper.

4. A process according to claim 3, wherein the enzymic reaction stopper is at least one member selected from the group consisting of decylsulfuric acid and salts thereof, dodecylsulfuric acid and salts thereof, and dodecylbenzenesulfonic acid and salts thereof.

5. A process for determining superoxide dismutase activity which comprises;
(i) producing superoxide anions by a method selected from the group consisting of (a) the reaction of xanthine with xanthine oxidase, (b) the use of a superoxidized compound, and (c) the reaction of a reduced form coenzyme with an electron carrier,
(ii) reacting superoxide dismutase with the superoxide anions produced in step (i) in the presence of an electron carrier and a maleimide and optionally, a carbonyl compound, to produce hydrogen peroxide, and
(iii) determining the amount of hydrogen peroxide produced therefrom colorimetrically wherein the amount of hydrogen peroxide produced is an indication of superoxide dismutase activity present.

6. A process according to claim 5, wherein the reaction of superoxide dismutase is carried out in the presence of an electron carrier, maleimide or a derivative thereof and a carbonyl compound.

7. A process according to claim 5, wherein the electron carrier is at least one member selected from the group consisting of phenazine methosulfate, 1-methoxy-5-methylphenazinium methylsulfate, and 9-dimethylaminobenzo-α-phenazoxonium chloride.

8. A process according to claim 5, wherein the determination of hydrogen peroxide is carried out colorimetrically by using a peroxidase and a color reagent after stopping the enzymic reaction or at the time of stopping the enzymic reaction by using an enzymic reaction stopper.

9. A process according to claim 8, wherein the enzymic reaction stopper is at least one member selected from the group consisting of decylsulfuric acid and salts thereof, dodecylsulfuric acid and salts thereof, and dodecylbenzenesulfonic acid and salts thereof.

10. A process according to claim 6, wherein the carbonyl compound is an aromatic ketone compound or an aliphatic ketone compound.

11. A process for determining superoxide dismutase activity which comprises;
(i) producing superoxide anions by a method selected from the group consisting of (a) the reaction of xanthine with xanthine oxidase, (b) the use of a superoxidized compound, and (c) the reaction of a reduced form coenzyme with an electron carrier,
(ii) reacting superoxide dismutase with the superoxide anions produced in step (i) in the presence of an electron carrier and a maleimide, a carbonyl compound and a member selected from the group consisting of bromine ions and citric acid or a salt thereof, to produce hydrogen peroxide, and
(iii) determining the amount of hydrogen peroxide produced therefrom colorimetrically wherein the amount of hydrogen peroxide produced is an indication of superoxide dismutase activity present.

12. A process according to claim 11, wherein the electron carrier is at least one member selected from the group consisting of phenazine methosulfate, 1-methoxy-5-methylphenazinium methylsulfate, and 9-dimethylaminobenzo-α-phenazoxonium chloride.

13. A process according to claim 11, wherein the determination of hydrogen peroxide is carried out colorimetrically by using a peroxidase and a color reagent after stopping the enzymic reaction or at the time of stopping the enzymic reaction by using an enzymic reaction stopper.

14. A process according to claim 13, wherein the enzymic reaction stopper is at least one member selected from the group consisting of decylsulfuric acid and salts thereof, dodecylsulfuric acid and salts thereof, and dodecylbenzenesulfonic acid and salts thereof.

15. A process according to claim 11, wherein the carbonyl compound is an aromatic ketone compound or an aliphatic ketone compound.

* * * * *